(12) United States Patent
Kwete (10) Patent No.: US 8,793,245 B2
(45) Date of Patent: Jul. 29, 2014

(54) PERSONALIZED MEDICAL TREATMENT PROVISION SOFTWARE

(71) Applicant: Patrick Kwete, Omaha, NE (US)

(72) Inventor: Patrick Kwete, Omaha, NE (US)

(*) Notice: Subject to any disclaimer, the term of this patent is extended or adjusted under 35 U.S.C. 154(b) by 9 days.

(21) Appl. No.: 13/625,756

(22) Filed: Sep. 24, 2012

(65) Prior Publication Data

US 2013/0080425 A1 Mar. 28, 2013

Related U.S. Application Data

(60) Provisional application No. 61/537,900, filed on Sep. 22, 2011.

(51) Int. Cl.
*G06F 17/30* (2006.01)
*G06F 19/00* (2011.01)

(52) U.S. Cl.
CPC .......... *G06F 19/322* (2013.01); *G06F 19/3443* (2013.01)
USPC .................... 707/723; 707/769; 707/E17.014

(58) Field of Classification Search
None
See application file for complete search history.

(56) References Cited

U.S. PATENT DOCUMENTS

| 6,151,581 | A | * | 11/2000 | Kraftson et al. | 705/3 |
| 2006/0052945 | A1 | * | 3/2006 | Rabinowitz et al. | 702/20 |
| 2010/0076786 | A1 | * | 3/2010 | Dalton et al. | 705/3 |

* cited by examiner

*Primary Examiner* — Anteneh Girma (57) ABSTRACT

A method for providing information exchange and analysis to a medical knowledge database that collects, organizes, and retrieves clinical experience information sets submitted by a plurality of treatment providers and researchers. The plurality of treatment providers and researchers submit clinical information containing biological sequences, signs and symptoms, and medical assessments to the database. the method searches the database for similar cases and if none are found, creates a new searchable case for the database and utilizes statistical calculations to determine an optimal treatment protocol, a treatment progression probability, and a patients personalized predicted medical future. The system accomplishes this through the use of a plurality of organizational and analysis methods that continually learns from its users, groups non-identical cases based on statistical similarities, performs sequence alignments on submitted biological sequences, utilizes pattern recognition software to determine similarities between medical images, and provides case follow ups to track treatment outcomes.

12 Claims, 10 Drawing Sheets

PERSONALIZED MEDICAL TREATMENT PROVISION SOFTWARE

The current application claims a priority to the U.S. Provisional Patent application Ser. No. 61/537,900 filed on Sep. 22, 2011. The current application is filed on Sep. 24, 2012 while Sep. 22, 2012 was on a weekend.

FIELD OF THE INVENTION

The present invention relates generally to an information exchange and analysis software method. More particularly to a software method utilized in a medical knowledge database that allows various health care providers, researchers, and clinical specialist to share their clinical experience to improve treatment selection, determine trends similar cases, and to compile a vast knowledge base with limitless research and analytical potential.

BACKGROUND OF THE INVENTION

Determining the best treatment protocol for a patient suffering from a rare condition is a complex process that largely relies on the availability and the dissemination of clinical research knowledge. In many instances, the dissemination and availability of clinical research knowledge is facilitated by the publication of clinical studies. These clinical studies provide a medical professional with invaluable information regarding a specific treatment protocol, the underlying conditions observed in a patient, and a documented outcome observed. This information is crucial for determining an optimal treatment protocol for a patient afflicted with a rare or new condition. While these clinical studies offer a wealth of knowledge, they suffer from several disadvantages that can potentially hinder the selection of the best treatment protocol.

One of the disadvantages associated with clinical studies is attributed to inescapable delay caused by publication. In some situation studies may conclude months or years prior to the publication of the results. Another disadvantage associated with clinical studies is the difficulty in accessing a plurality of closely related clinical studies that published through different scientific journals. Currently, clinical studies and journal article are allowed to be restricted to a particular publication for a period of one year, after which the clinical study or journal article is made available for public viewing. Both of these disadvantages create a gap in information availability that hinders treatment providers. Still another disadvantage associated with clinical studies is attributed to the specificity of a particular study. In some cases several clinical studies may be conducted for a condition with a specific treatment protocol, but due to the specificity of the particular clinical study, the information becomes difficult to utilize. To improve upon this disadvantage a plurality of clinical information databases have been developed that offer an improved method to locate and identify similar conditions and optimal treatments from a vast publication database of clinical studies. While this solution improves upon some of the current disadvantages associated with finding clinical information, the gap in information availability is still present.

Therefore it is the object of present invention to improve the current provides a medical knowledge database and an information exchange and analysis software method that collects, organizes, and retrieves clinical experience submitted by various health care providers, researchers, and clinical specialist for the purpose of determining an optimal treatment protocols for new or existing conditions, as well as for predicting the medical future and a treatment progression for a patient afflicted with a particular condition or disorder.

DETAIL DESCRIPTIONS OF THE INVENTION

Figure 1:
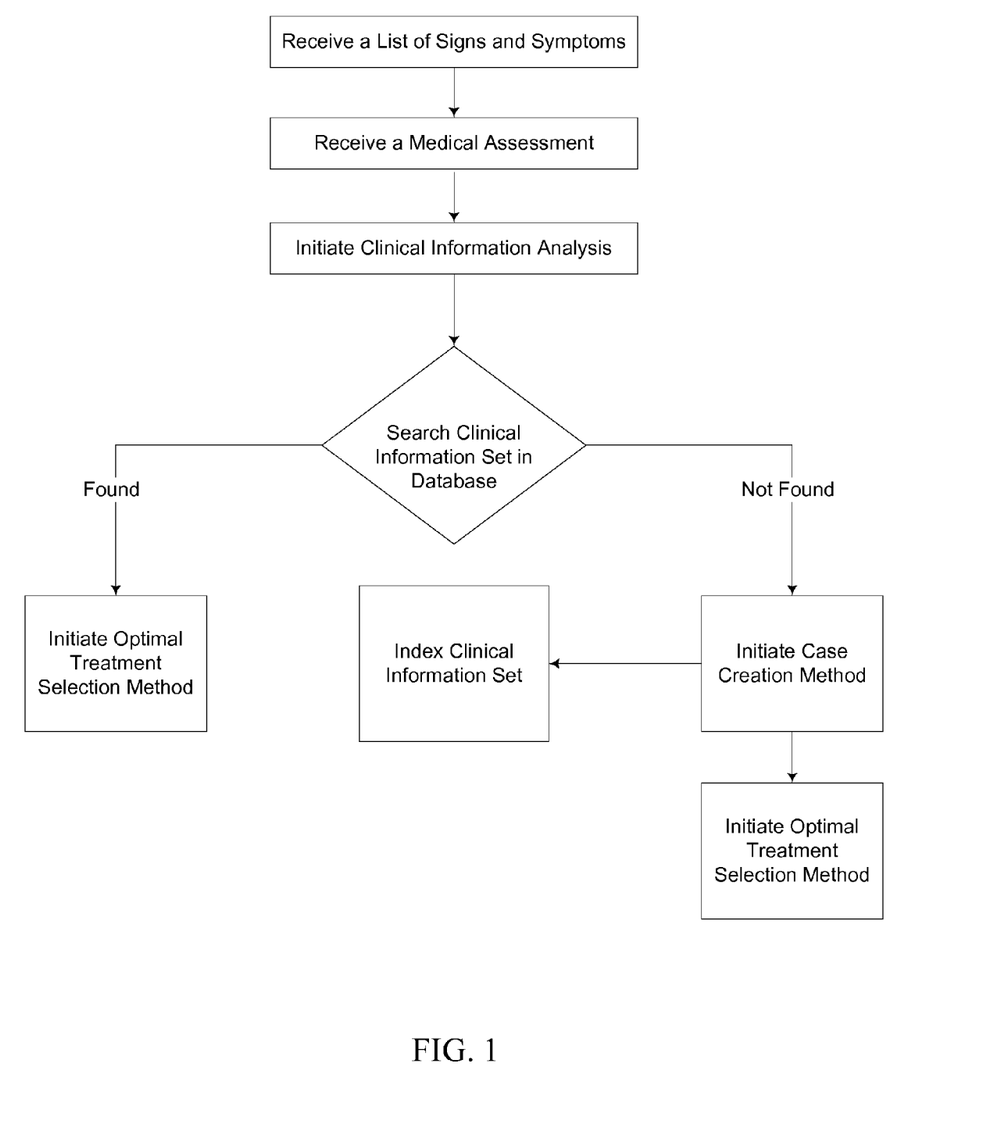
FIG. 1 is flow chart diagram illustrating the initiation of an optimal treatment selection method utilizing a clinical information analysis case.
Figure 2:
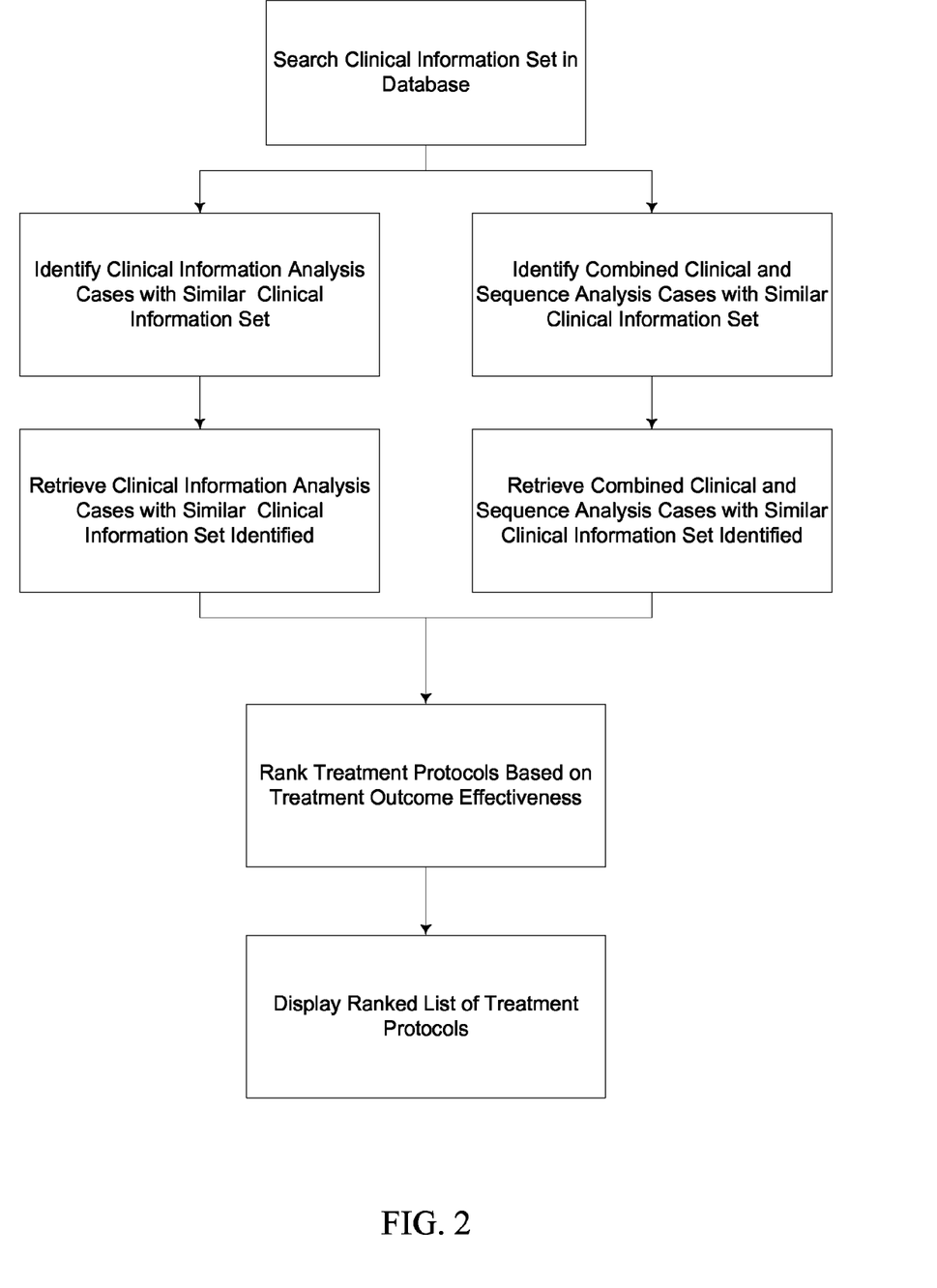
FIG. 2 is a flow chart diagram illustrating the continuation of an optimal treatment selection method utilizing a clinical information analysis case and having identified matching clinical information set in the database.
Figure 3:
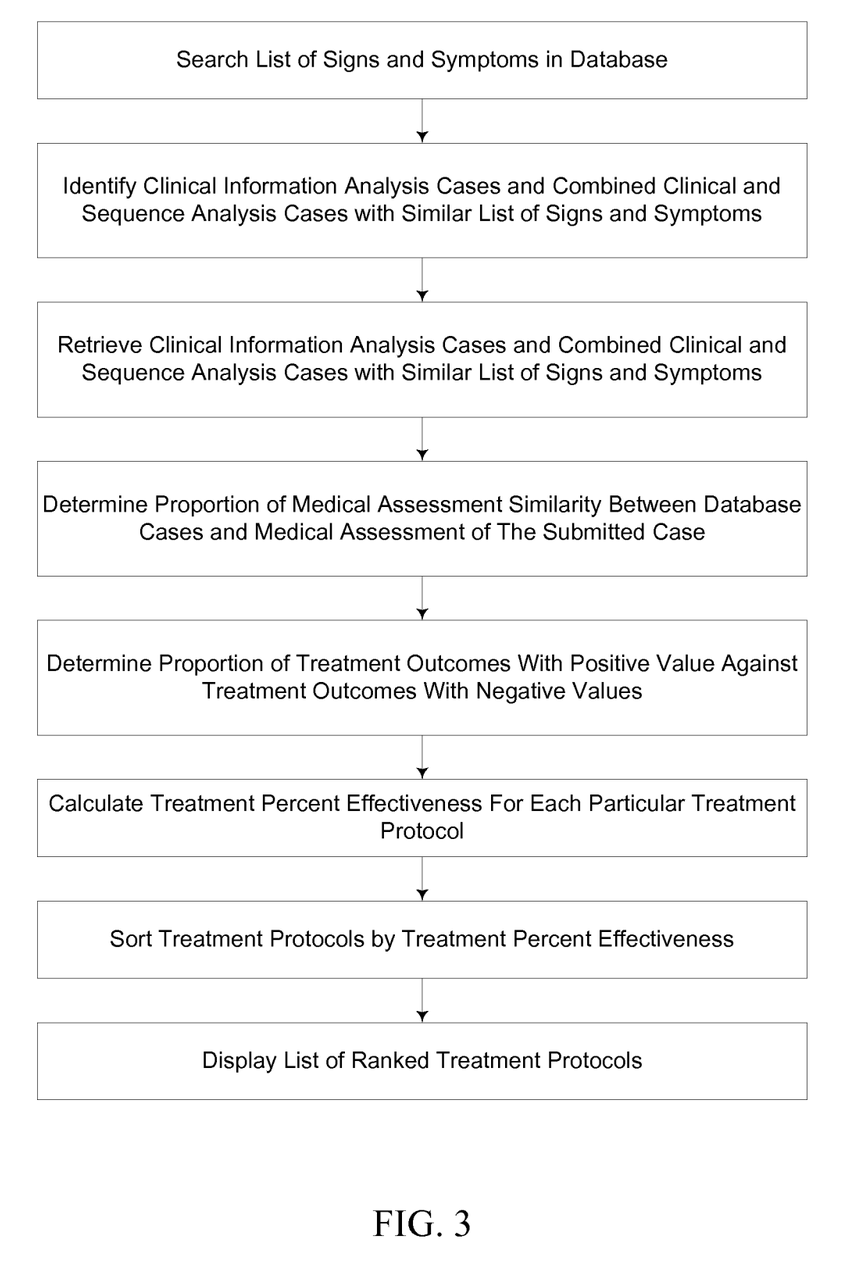
FIG. 3 is a flow chart diagram illustrating the continuation of an optimal treatment selection method utilizing a clinical information analysis case and having not identified matching clinical information set in the database.
Figure 4:
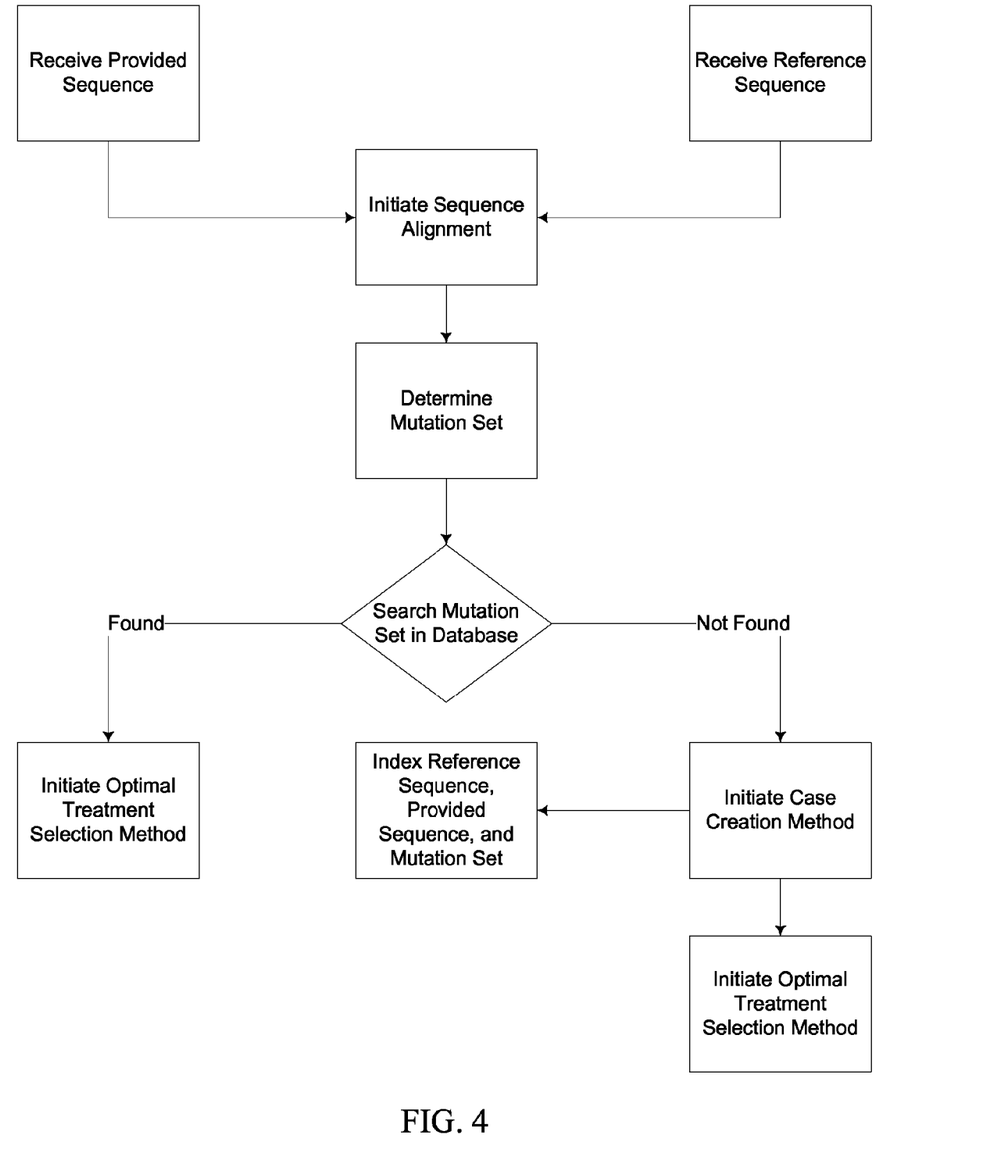
FIG. 4 is flow chart illustrating the initiation of an optimal treatment selection method utilizing a sequence analysis case.
Figure 5:
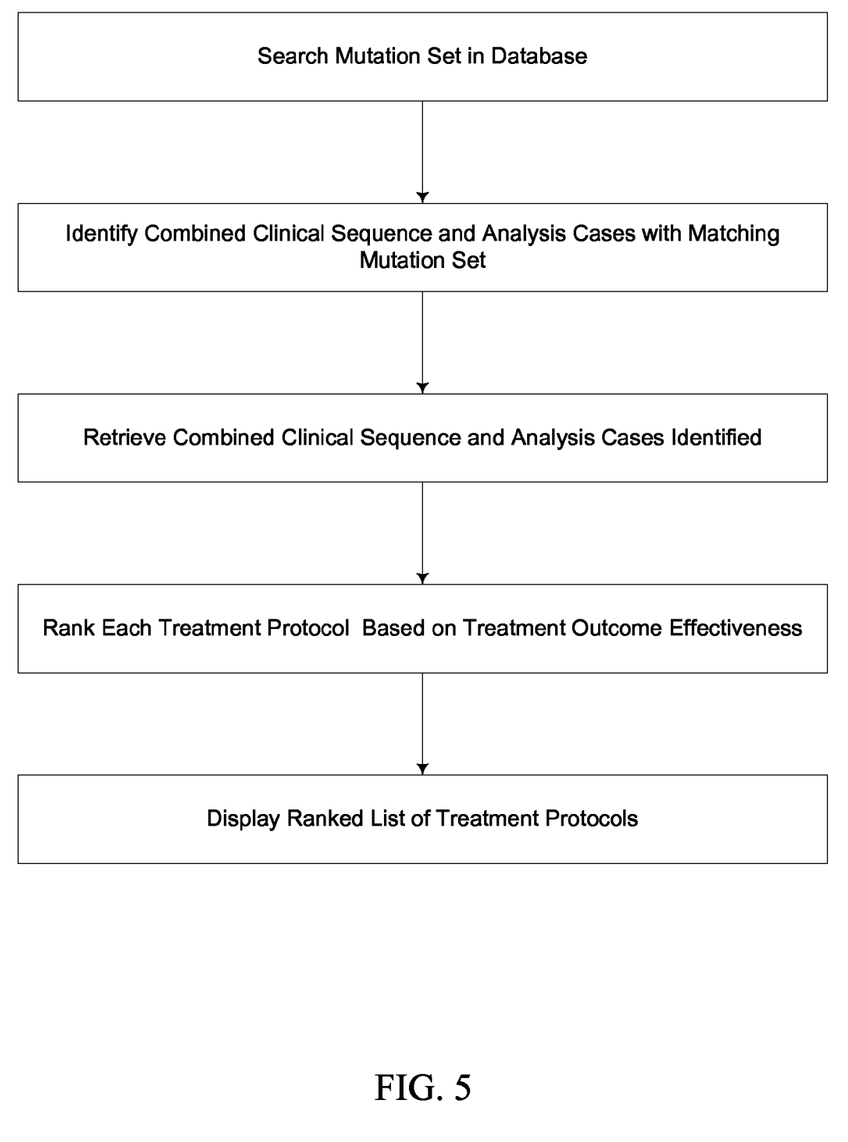
FIG. 5 is a flow chart diagram illustrating the continuation of an optimal treatment selection method utilizing a sequence analysis case and having identified a matching mutation set in the database.
Figure 6:
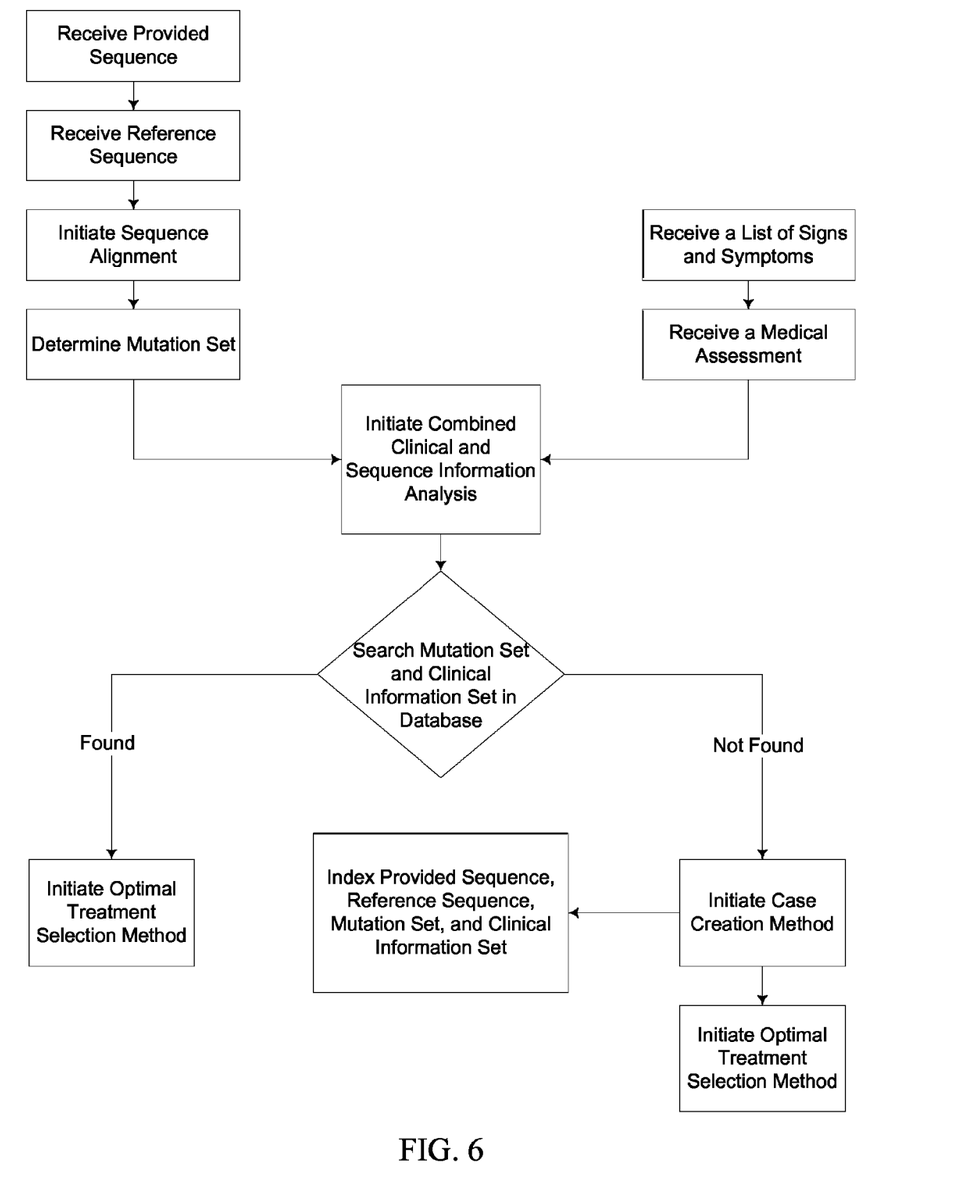
FIG. 6 is flow chart diagram illustrating the initiation of an optimal treatment selection method utilizing a combined clinical and sequence analysis case.
Figure 7:
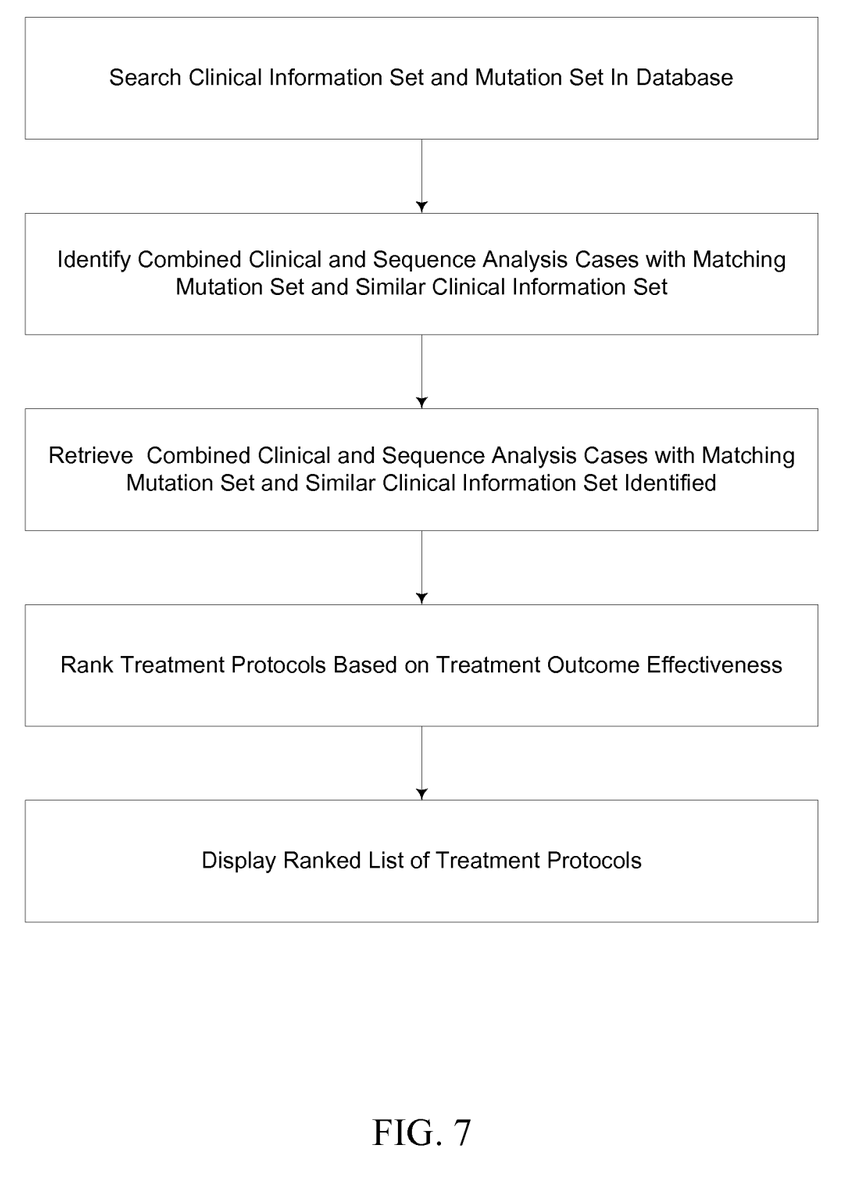
FIG. 7 is a flow chart diagram illustrating the continuation of an optimal treatment selection method utilizing a combined clinical and sequence analysis case and having identified a matching mutation set and clinical information set in the database.
Figure 8:
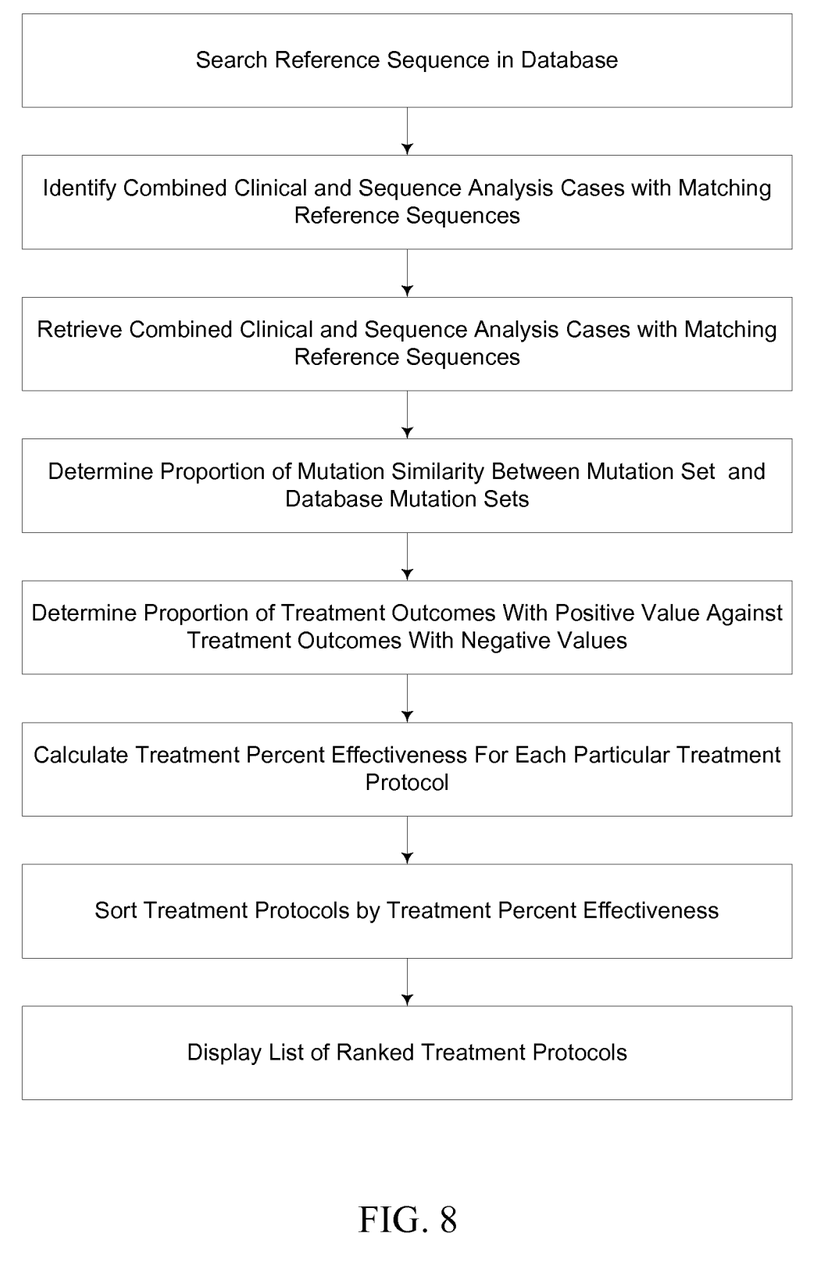
FIG. 8 is a flow chart diagram illustrating the continuation of an optimal treatment selection method utilizing either a sequence analysis case or a combined clinical and sequence analysis case and having not identified a matching mutation set in the database.
Figure 9:
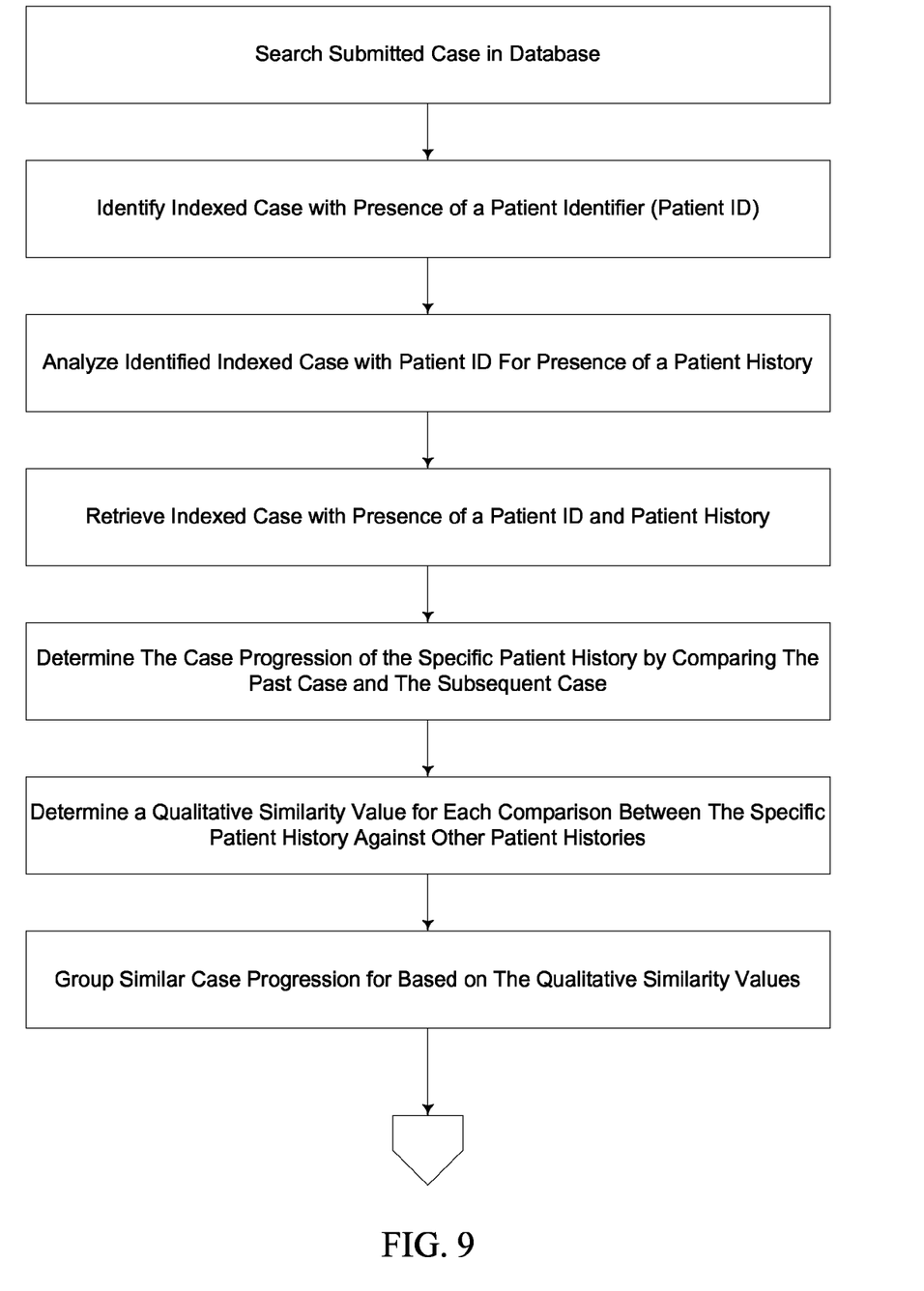
FIG. 9 is flow chart illustrating the initiation of a case progression method utilizing a combined clinical and sequence analysis case.
Figure 10:
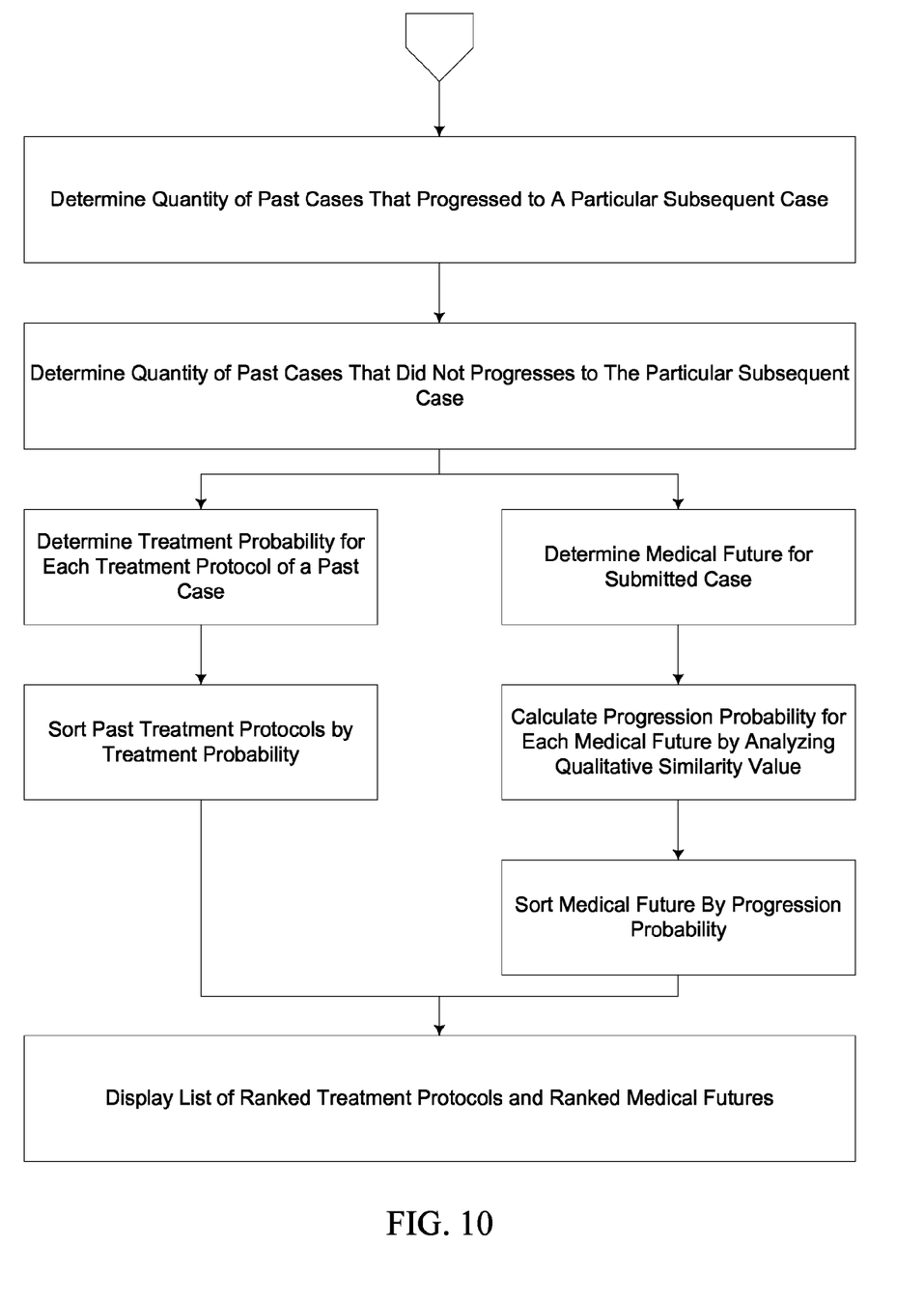
FIG. 10 is flow chart illustrating the continuation of a case progression method utilizing a combined clinical and sequence analysis case.

All illustrations of the drawings are for the purpose of describing selected versions of the present invention and are not intended to limit the scope of the present invention.

The present invention is an information exchange and analysis software method utilized in a medical knowledge database that collects, organizes, and analyzes a plurality of clinical experience. The method used by the system allows treatment providers, clinical researchers, and treatment specialists with an analytical tool that is capable of performing sequence alignments, determining an optimal treatment protocol, and predicting the progression of a case based on submitted sequence and clinical information provided by the treatment providers, clinical researchers, or treatment specialists. It should be noted that references to treatment providers, clinical researchers, and treatment specialists are hereinafter collectively referred to as users. The present invention accomplishes this through the use of a software system that aggregates and organizes a plurality of clinical experiences provided by users. The system categorizes the plurality of clinical experiences into three case structures. These case structures are determined by the information contained within each of the plurality of clinical experiences when they are submitted. The system detects the presence of new information and creates a new case for the database. The system detects similarities between non-identical cases based on determined statistical similarities. The system groups cases based on the presence of a patient identifier that allows case information to be updated providing improved information consolidation and permitting facilitated statistical analysis between cases. The system provides and update function that combines all the knowledge obtained from different users.

The database receives a plurality of clinical experiences that are organized into three case structures. The three case structures stored within the database comprises a plurality of sequence analysis cases, a plurality of clinical information analysis cases, and a plurality of combined clinical and sequence analysis cases. The plurality of sequence analysis cases comprises a provided sequence, a reference sequence, and a mutation set. The mutation set comprises a plurality of mutations. The plurality of clinical information analysis cases comprises a clinical information set, a treatment protocol, and a treatment outcome. The clinical information set comprises a list of signs and symptoms and a medical assessment. The plurality of combined clinical and sequence analysis cases comprises a provided sequence, a reference sequence, a mutation set, a clinical information set, a treatment protocol, and a treatment outcome.

The system utilizes a plurality of grouping and organizational methods to provide the system with improved information recall and facilitated access for information analysis. The plurality of grouping and organizational methods utilized by the system comprises a case creation method, a statistically driven non identical case grouping method, and a patient identifier grouping method. The case creation method analyzes the plurality of clinical experiences submitted to the system and detects the presence of new information to create a new case structure with the system utilizing the submitted data. The statistically driven non identical case grouping method detects statistical similarities between the plurality of combined clinical and sequence analysis cases in the database by comparing the clinical information sets of each. The patient identifier grouping method provides the user with the ability to open a patient electronic health record which creates a new combined clinical and sequence analysis case containing a patient identifier which allows the system to track and update the patient's health record as well as provides the system with the creation of a patient history for determining case progressions.

The system comprises a plurality of computational methods that analyze the plurality of clinical experiences that are submitted to the database. The plurality of computational methods comprises a sequence analysis method, an optimal treatment selection method, and a case progression prediction method. The sequence alignment method utilizes the provided sequence and the reference sequence to perform a sequence alignment between the two. The provided sequence comprises a biological sequence, wherein the biological sequence is a genomic sequence, an amino acid sequence, or an RNA sequence. The reference sequence comprises a biological sequence wherein the biological sequence is a genomic sequence, an amino acid sequence, or an RNA sequence. The provided sequence and the reference sequence must both either be a nucleotide sequence or an amino acid sequence. The optimal treatment selection method utilizes clinical information sets or biological sequence information to determine a treatment protocol with the highest success rate for the searched clinical information set or biological sequence. The optimal treatment selection method can determine an optimal treatment through a direct case match between the provided case information or through an optimum seeking selection process that utilizes case similarities between the submitted case information and the indexed cases. Furthermore the system provides a case progression method, wherein the system determines the treatment protocols with the fewest subsequent conditions as well as determines the treatment protocols with the lowest probability for causing a subsequent condition. The determination of subsequent conditions is related to the likelihood of progressing into a subsequent case.

The sequence analysis for the system provides the system with a sequence alignment. The sequence analysis is preformed when the system receives the reference sequence and the provided sequence. The system then initiates the sequence alignment algorithm which performs a global alignment between the reference sequence and the provided sequence. The global alignment attempts to align every residue between the provided and the reference sequence according to a similarity matrix which determines values for a match, a particular mismatch, and for a gap. The highest total score determines the best possible alignment between to sequences. The sequence alignment identifies the set of mutations, insertions and deletions present in the provided sequence. The set of mutation, insertions and deletions are combined and referred to as the mutation set for the particular combination of the provided sequence and the particular reference sequence.

The optimal treatment selection method can be determined by searching a particular mutation set or a particular clinical information set in the database. The optimal treatment selection method functions as an independent search feature or as an additional analysis function preformed in conjunction with a sequence analysis for a sequence analysis case or a combined clinical and sequence analysis case, as well as part of clinical information analysis.

The optimal treatment selection method can be performed for the sequence analysis cases and the combined clinical and sequence analysis cases because mutation sets found in genomic sequences, protein sequences, RNA sequences are associated with the particular manifestations of a disease or condition as well as particular treatment protocols with quantified treatment outcomes. Through directly matching a searched mutation set with the mutation sets of the plurality of combined clinical and sequence analysis cases in the database, an optimal treatment protocol can be determined. Initiation of the optimal treatment selection method begins with a database search utilizing the mutation set as the search parameters. In the situation where the system detects a match for the searched mutation set, the system would retrieve the plurality of combined clinical and sequence analysis cases that contain a matched mutation set. The system then analyzes the treatment outcomes of each of the plurality of combined clinical and sequence analysis cases. The treatment protocols are then ranked according to the successfulness of the treatment outcome. The system then displays the results to the users as a ranked list.

In the situation where the system does not detect a match for the searched mutation set, the system would retrieve the plurality of combined clinical and sequence analysis cases from the database that utilized the same reference sequence as the mutation set searched. The system would use the retrieved combined clinical and sequence analysis cases to calculate a predicted treatment optimal based on percent similarities between the cases. The reference sequence is used as a case identifier by the system which retrieves the plurality of combined clinical and sequence analysis cases. The system then searches each of the combined clinical and sequence analysis cases to detect the plurality of mutations for which the treatment outcomes are successful. The system then searches each of the combined clinical and sequence analysis cases to detect the plurality of mutations for which the treatment outcomes are not successful. Based on the proportion of the similarities for each of the plurality of mutations of each group analyzed compared to the plurality of mutations in the searched mutation set, a percentage is calculated for each of the associated treatment protocol based on the rate of success and the percent commonality between the plurality of mutations of the submitted mutation set and the plurality of mutations from the searched mutation sets in the database.

The optimal treatment selection method can be performed on the plurality of clinical experiences that do not contain biological sequence information. The optimal treatment selection method can be implemented while conducting a clinical information analysis or can be conducted independently. Initiation of the optimal treatment selection method begins with a database search utilizing a clinical information set as the search parameters. In the situation where the clinical information set searched is matched to the clinical information sets of the plurality of clinical information analysis cases and the combined clinical and sequence analysis cases, the system determines the optimal treatment protocol based on the successfulness of the treatment outcome. The system ranks each of treatment protocols based on the successfulness of the treatment outcome and then displays the rankings as a list to be view by the user.

In the situation where the clinical information set search is not matched to the clinical information sets of the plurality of clinical information analysis cases and the combined clinical and sequence analysis cases, the system searches the database utilizing the list of signs and symptoms. The system retrieves the plurality of clinical information analysis cases and the plurality of combined clinical and sequence analysis cases that match or are similar to the list of signs and symptom searched. The system determines the similarities between the medical assessments of the plurality of clinical information analysis cases and the plurality of combined clinical and sequence analysis cases to the medical assessment of the clinical information set searched. The system then determines the proportion of positive treatment outcomes against the proportion of negative treatment outcomes in order to calculate a treatment percent effectiveness for each treatment protocol. The system ranks the treatment protocols based on treatment percent effectiveness and displays the list to the user.

The case progression prediction method is utilized to determine a potential case progression for a particular case based on the progression of indexed cases within the system determined to have commonality with the particular case. The system can determine the progression of a searched case as an independent analysis or as a prediction based on a treatment protocol. The system can determine the progression probability by matching a searched case to an indexed case with a patient history. The patient history provides a subsequent case for which a predicted case progression can be determined.

The system can also determine the case progression of a searched cased based on calculations that determine a quantitative value for qualitative similarities between cases. The case progression prediction method commences when a new clinical experience is received containing a reference sequence, a provided sequence, and a clinical information set. The system utilizes the provided sequence and the reference sequence to conduct a sequence alignment which provides the system with a mutation set. The system initiates a database search utilizing the clinical information set received and the mutation set of the sequence alignment as search terms. The system searches indexed cases that have patient identifiers. The system further determines a past case and a subsequent case for each indexed case with a patient identifier. The determination of a past case and a subsequent case provides the system with the ability to group the cases as part of a patient history under a particular patient identifier. The system then compares the past cases with the clinical information set received and the mutation set from the sequence alignment. It should be noted that references to the clinical information set received and the mutation set from the sequence alignment is hereinafter referred to as the submitted case unless otherwise noted.

The system retrieves the indexed cases containing a patient history with a past case matching the submitted case. The system calculates the percent similarity between the submitted case and the past case. The system then determines a case progression for each of the patient histories by comparing the past case against their subsequent case. To accomplish this, the system creates subsequent case types by grouping subsequent cases based on similarities that are determined by the system. The system determines a progression probability for each subsequent case type observed by determining a positive progression value for each subsequent case type and a negative progression value for each subsequent case type. The positive progression value is the quantity of past cases that progressed into a particular subsequent case type, while the negative progression value is the quantity of past cases that did not progress into the particular subsequent case type. the system then calculates the treatment probability for each treatment protocol utilized by a past case by calculating the instance a particular treatment protocol, utilized in a past case, was associated with a particular subsequent case type and the instances the particular treatment protocol, utilized in a past case, was not associated with a particular case type. The system then determines a personalized predicted medical future for particular case observed by the system with the probability of the likelihood of the observed cases progressing into the particular subsequent case. The system calculates a progression probability for each of the medical futures by comparing the past case to the submitted case and determining the ranking based on a similarity value. The system sorts the medical futures by the progression probability. The system then displays a list of the treatment protocols ranked by the treatment probability, and a list of the medical futures ranked by the progression probability.

In the preferred embodiment of the present invention the mutation set and the clinical information set which comprise the submitted case are referred to in the claims as the new search case. The database is described as comprising a plurality of patient histories. The patient histories comprise a past case and a subsequent case wherein the past case and the subsequent case contain a matching patient identifier. Moreover it should be noted that the case progression from the past case to the subsequent case can be referred to as a whole as the patient history, wherein the patient history is the progression as well as the combined entity of the past case and the subsequent case. Still furthermore it should be noted that a patient similar value is used to determine the percent similarity between each of the past cases of the patient histories retrieved and the new search case, wherein the patient similar value is calculated based on the weighted values for the information contained within the clinical information set and the values for the information contained. It should also be noted the qualitative similarity value is also calculated for the plurality of patient histories to determine the similarities between each of the patient histories to one another. The qualitative similarity value is used to group patient histories based on similar case progressions and to determine the value of the percentage of a particular occurrence of a subsequent case from the retrieved values collected. Furthermore it should be noted that the treatment progression probability is used interchangeably with the treatment occurrence probability. The treatment occurrence probability is the instance that a particular treatment protocol appears associated with a particular grouping of subsequent cases which can be interpreted as being related to similar patient histories. It should also be noted that the medical futures, as described, are the specific case progression for a particular case progression but can be interpreted as being a grouping of similar case progressions. Moreover it should be noted that medical futures are used interchangeably with case progression except that medical futures are used to describe the qualitative aspects while case progression are used to describe the more quantitative aspects, even though both interpretations describe the progression of a past case to a subsequent case or the grouping of similar progression to the particular to subsequent case.

In the preferred embodiment of the present invention, the method utilizes a plurality of biological sequences for sequence alignments and information analysis. The biological sequences can comprise amino acid sequence, genomic sequences, and RNA sequences. In order to conduct the sequence alignment, the provided sequence and the reference sequence must be entered in a FASTA format. The reference sequence used in performing a sequence alignment can be provided by the user or the user can select the reference sequence from a list of reference sequences collected in the database. If the system does not detect the reference sequence in the database, the system stores the reference sequence. Furthermore, the system performs the sequence alignment by performing global alignments on the provided sequences against a selected or submitted reference sequence. The sequence alignment identifies the set of mutations, insertions and deletions present in the provided sequences.

In the present invention, the clinical information analysis method utilizes a clinical information set that comprises a list of signs and symptoms and a medical assessment. The list of signs and symptom comprises a list of currently expressed symptoms, medical test results, such as radiology reports, imaging scans, and any biomarkers. The medical assessment comprises the patient's age, weight, and length of illness, but additionally includes any information regarding the patient's current state. Furthermore it should be noted that scalar values associated with a patient's medical assessment are weighted and placed in a range group to provide facilitated indexing and analysis options. The system can identify the patterns for qualitative values through the use of a pattern recognition algorithm. The pattern recognition algorithm can be used to identify a qualitative similarity value which can be used to identify proportional similarities through global or local means within a data set. Furthermore the pattern recognition algorithm can provide a means to identify trends in medical imagining results.

In the present invention, the system displays genomic sequences, RNA sequences, protein sequences related to a particular clinical information analysis performed in graphical formats. The system utilizes the mutation sets associated with a particular condition and determined the treatment protocols ranked by percent effectiveness in a bipartite graph. The present invention allows users to view how treatment protocols success varies as a result of information variations caused by a lack of information availability or case dissimilarities.

In the present invention, the clinical information analysis cases are created according to the conditions based on the list of signs and symptoms, but can also be created with respect to changes in the medical assessment that includes changes to the patient's age, weight, and length of illness. Additionally, the clinical information analysis cases can be created due to differences in patient histories where a past case contains treatment outcomes as well as treatment protocols that have been used for the relevant conditions as well as any current treatment being used for the similar conditions. Furthermore, the present invention can detect case similarities between cases in the database. It does this by comparing submitted clinical information against the clinical information within clinical information analysis cases in the database. The system compares the data sets for any patterns or similarities and creates a new database case if none are detected. The system then updates its method for detecting new patterns to include the new case.

In the present invention the optimal treatment selection method utilizes a percentage calculation for determining the optimal treatment protocol for a submitted mutation set based on the similarities between the plurality of mutation in the indexed cases and the plurality of mutation in of the searched mutation set. The system accomplishes by calculating percent effectiveness for a particular treatment based on mutation set similarity. As well as treatment effectiveness for each treatment observed with a particular proportion of mutations in the mutation set. To calculate the treatment effectiveness the system divide the number of mutations present in the mutation set submitted for analysis that are found in the set of all mutations (of the respective reference sequence) for which the treatment in question is reported to be effective for, denoted as the variable x, by the total number of mutations in this set, denoted as the variable y. the system also divides the number of mutations present in the mutation set submitted for analysis that are found in the set of all mutations (of the respective reference sequence) for which the treatment in question is reported to be ineffective for, denoted as the variable z, by the total number of mutations in this set, denoted as the variable q.

$$\text{Percentage}=(x/y-z/q)*100$$

In the present invention, the system is able to keep track of the occurrence of particular case globally, everywhere it is being accessed, as well as locally, at which location it is being accessed. The system record the date and time a case was created as well as the date and time a case was first accessed by another user. The system provides this to continuously learn from its users. Additionally, case information can be either obtained by utilizing the system to perform an analysis or by creating a patient electronic health record. In both situations, the system continues to learn from its user's experiences. By using an electronic health record a patient's case is associated with a patient id which provides users with the ability to update the patient's case information. A user is able to update a patient's electronic health record by entering a patient id number in the system and updating the outcome for a particular treatment protocol, such as any side effects observed for the treatment, therapy, and/or drugs used. The summation of the outcomes for a treatment protocol to a case is used as a weight for a particular treatment protocol for a case type of condition. The systems feature allows users to add treatments, therapies, drugs and/or remedies but additionally provides the ability to add new genomic sequences, RNA sequences, amino acid sequences as reference sequences for analysis.

In the present invention the treatment protocol are provided as a group of variables that are ungrouped with the list of signs and symptoms or the medical assessment. In alternative embodiment of the present invention the treatment protocols can be grouped with either the list of signs and symptoms or the medical assessment to provide the system with the ability to have a feedback loop or cycle. This feature would occur at the end of the cycle.

In the present invention the system is able to update the present invention comprises of a knowledgebase updating algorithm that allows the present invention to be updated without the use of the internet or network if necessary. The algorithm allows the present invention to combine all the knowledge obtained from its different users. At update the knowledge of the user and another user ('the headquarters'), both users acquires all new cases (mutation sets, clinical information and mutation sets as well as clinical information), makes the appropriate re-evaluation of cases in common (i.e. likely side effects, treatment efficiency), acquires all new treatments in use, all reference sequences in use. The system also lets a user know what genomic sequences, RNA sequences, protein sequences are relevant to a subjects based on their clinical information. It uses knowledge in its knowledgebase to do this. The present invention allows users to view how different mutation set 'cases' affect the different therapies, treatments and/or regimes graphically, as a graph of cases and treatments, and the mutations in each mutation set.

In the present invention, the system is able to determine case progression prediction on a new submitted cased by comparing the progression of indexed cases in the database. The system accomplishes this by determining a proportional similarity of the indexed case to the submitted case and calculating the likelihood that the submitted case will progress to a subsequent case as well as at what time point (age) this progression will occur. The present invention can give theses a case progression prediction probability and a possible medical future which can be displayed in a combined map. The system is capable of accomplishing this because the number of conditions is finite and the number of individuals with any condition at any time point is finite. it follows that the system's method of continuous piecewise and reassembly learning at a subsequent time point gains information for a greater set of the finite piece in each 'case' at a subsequent time point. Hence, it follows that with continuous use, the number of subjects in each 'case' either elapses or continues to progress. If the number of subjects in the case elapses, it follows that they where finite. Hence, it must be that the information acquired by the database is the most accurate depiction for that case from the point at which it was put in use. However, if the subjects in a case do not elapse, then they must be infinite. If they are infinite, then the effect of each treatment, regime and/or side effects is simply the limit as the number of subjects approaches infinity; it must either converge or diverge. The present invention can analyze the progression of information in its database to determine if information is converging or diverging. If it is converging, then the database depicts the accurate information for that case as well. If it diverges then the database still contains the most accurate information for the case that it diverges. Since this is true for one 'case' in the database, by the induction hypothesis it is clearly true for all 'cases' in the database.

Although the invention has been explained in relation to its preferred embodiment, it is to be understood that many other possible modifications and variations can be made without departing from the spirit and scope of the invention as hereinafter claimed.

What is claimed is:

1. A method for conducting an optimal treatment protocol selection and determining case progression by executing computer-executable instructions stored on a non-transitory computer-readable medium, the method comprises the steps of:

providing a plurality of searchable cases stored within a database, wherein the database is a knowledge base;

receiving a plurality of new clinical experiences, wherein each of the plurality of new clinical experiences comprises a plurality of nucleotide sequences, a plurality of amino acid sequences, a clinical information set, a treatment protocol, and a treatment outcome;

creating new searchable cases from the plurality of new clinical experiences by way of a case creation method;

indexing the new searchable cases and the plurality of searchable cases;

organizing the plurality of searchable cases for facilitated retrieval and analysis, wherein the searchable cases comprise a sequence analysis case and a combined clinical and sequence analysis case;

wherein the sequence analysis case and the combined clinical and sequence analysis case each comprise a provided sequence, a reference sequence, and a mutation set;

wherein the combined clinical and sequence analysis case further comprises a clinical information set, a treatment protocol, and a treatment outcome;

performing a sequence analysis on the plurality of new clinical experiences by way of a sequence alignment algorithm; and selecting a treatment protocol based on the plurality of new clinical experiences by performing an optimal treatment selection method.

2. The method for conducting an optimal treatment protocol selection and determining case progression by executing computer executable instructions stored on a non-transitory computer readable medium, the method as claimed in claim 1 comprises the steps of:

receiving a new clinical experience, wherein the new clinical experience contains the plurality of nucleotide sequences or the plurality of amino acid sequences formatted as the reference sequence and the provided sequence;

initiating the sequence alignment algorithm in order to create a sequence alignment from the provided sequence and the reference sequence;

determining the mutation set from the sequence alignment, wherein the mutation set comprises a plurality of mutations;

initiating the optimal treatment selection method; and searching the mutation set in the database.

3. The method for conducting an optimal treatment protocol selection and determining case progression by executing computer executable instructions stored on a non-transitory computer readable medium, the method as claimed in claim 2 comprises the steps of:

retrieving the combined clinical and sequence analysis cases from the database, if the combined clinical and sequence analysis cases in the database contains a particular mutation set matching the mutation set of the sequence alignment;

ranking the treatment protocol by the treatment outcome for each of the combined clinical and sequence analysis cases retrieved from the database in order to compile a list of ranked treatment protocols; and displaying the list of ranked treatment protocols.

4. The method for conducting an optimal treatment protocol selection and determining case progression by executing computer executable instructions stored on a non-transitory computer readable medium, the method as claimed in claim 2 comprises the steps of:

initiating the case creation method, if the combined clinical and sequence analysis cases and the sequence analysis cases in the database do not contain the particular mutation set matching the mutation set of the sequence alignment;

indexing the provided sequence, the reference sequence, the mutation set, the clinical information set, the treatment protocol, and the treatment outcome of the new clinical experience as a new combined clinical and sequence analysis case,     if the new clinical experience consists of the provided sequence, the reference sequence, the clinical information sets, the treatment protocols, and the treatment outcomes;

indexing the provided sequence, the reference sequence, and the mutation set of the new clinical experience as a new sequence analysis case,     if the new clinical experience consists of the provided sequence and the reference sequence;

searching the database for the combined clinical and sequence analysis cases containing a particular reference sequence matching the reference sequence of the new combined clinical and sequence analysis case, wherein in the new combined clinical and sequence analysis case is excluded from the search;

retrieving the combined clinical and sequence analysis cases containing a particular reference sequence matching the reference sequence of the new combined clinical and sequence analysis case from the database;

determining a mutation proportionality between the plurality of mutations of the new combined clinical and sequence analysis case and the plurality of mutations of the combined clinical and sequence analysis cases;

determining a treatment proportionality between the treatment outcomes with a positive value against the treatment outcomes with a negative value for the combined clinical and sequence analysis cases;

calculating a treatment percent effectiveness by differentiating the mutation proportionality and the treatment proportionality and multiplying by one hundred;

ranking the treatment protocol by the treatment percent effectiveness for each of the combined clinical and sequence analysis cases retrieved from the database in order to compile a list of ranked treatment protocols; and     displaying the list of ranked treatment protocols.

5. A method for conducting a clinical information analysis for determining an optimal treatment selection by executing computer-executable instructions stored on a non-transitory computer-readable medium, the method comprises the steps of:

providing a plurality of searchable cases stored within a database, wherein the database is a knowledge base;

receiving a plurality of new clinical experiences, wherein each of the plurality of new clinical experiences comprises a plurality of nucleotide sequences, a plurality of amino acid sequences, a clinical information set, a treatment protocol, and a treatment outcome;

creating new searchable cases from the plurality of new clinical experiences by way of a case creation method;

indexing the new searchable cases and the plurality of searchable cases;

organizing the plurality of searchable cases for facilitated retrieval and analysis, wherein the plurality of searchable cases comprises a clinical information analysis case and a combined clinical and sequence analysis case;

wherein the clinical information analysis case and the combined clinical and sequence analysis case each comprise a list of signs and symptoms, a medical assessment, a treatment protocol, and a treatment outcome;

wherein the combined clinical and sequence analysis case further comprises a provided sequence, a reference sequence, and a mutation set;

determining a qualitative similarity value between the plurality of searchable cases by initiating a pattern recognition algorithm; and     selecting an optimal treatment based on the plurality of new clinical experiences by performing an optimal treatment selection method.

6. The method for conducting a clinical information analysis for determining an optimal treatment selection by executing computer executable instructions stored on a non-transitory computer readable medium, the method as claimed in claim 5 comprises the steps of:

receiving a new clinical experience, wherein the new clinical experience comprises a clinical information set, the treatment protocol, and the treatment outcome;

wherein the clinical information set comprises the list of signs and symptoms and the medical assessment;

initiating the optimal treatment selection method; and searching the clinical information set in the database.

7. The method for conducting a clinical information analysis for determining an optimal treatment selection by executing computer executable instructions stored on a non-transitory computer readable medium, the method as claimed in claim 6 comprises the steps of:

retrieving the plurality of searchable cases from the database,     if the plurality of searchable cases in the database contain a particular clinical information set matching the clinical information set of the new clinical experience;

ranking the treatment protocol by the treatment outcome for each of the plurality of new searchable cases retrieved from the database in order to compile a list of ranked treatment protocols; and     displaying the list of ranked treatment protocols.

8. The method for conducting a clinical information analysis for determining an optimal treatment selection by executing computer executable instructions stored on a non-transitory computer readable medium, the method as claimed in claim 6 comprises the steps of:

initiating the case creation method, if the plurality of searchable cases in the database do not contain the particular clinical information set matching the clinical information set of the new clinical experience;

indexing the clinical information set, the treatment protocol, and the treatment outcome of the new clinical experience as a new clinical information analysis case;

searching the database for the plurality of searchable cases containing a particular list of signs and symptoms matching the list of signs and symptoms of the new clinical information analysis case, wherein the new clinical information analysis case is excluded from the search;

retrieving the plurality of searchable cases containing the particular list of signs and symptoms matching the list of signs and symptoms of the new clinical information analysis case;

comparing medical assessment of each of the plurality of searchable cases matching the particular list of signs and symptoms against the medical assessment of the new clinical information analysis case to generate the qualitative similarity values by way of the pattern recognition algorithm;

determining a treatment proportionality between the treatment outcomes with a positive value against the treatment outcomes with a negative value for the plurality of searchable cases matching the particular list of signs and symptoms;

calculating a treatment percent effectiveness for each treatment protocol by differentiating the value of the treatment proportionality from the value of the qualitative similarity value and multiplying by one hundred;

ranking the treatment protocol by the treatment percent effectiveness for each of the plurality of searchable cases from the database in order to compile a list of ranked treatment protocols; and displaying the list of ranked treatment protocols.

9. A method for determining the case progression for a new clinical experience by executing computer-executable instructions stored on a non-transitory computer-readable medium, the method comprises the steps of:

providing a plurality of patient histories stored within a database, wherein the database is a knowledge base;

receiving a plurality of new clinical experiences, wherein each of the plurality of new clinical experiences comprise a patient identifier, a reference sequence, a provided sequence, a sign and symptom, a medical assessment, a treatment protocol, and a treatment outcome;

organizing the plurality of patient histories for facilitated search and analysis;

wherein each of the patient histories comprises a past case and a subsequent case;

wherein the past case and the subsequent case each comprise a provided sequence, a reference sequence, a mutation set, a list of signs and symptoms, a medical assessment, a treatment protocol, a treatment outcome, and a matching patient identifier;

performing a sequence analysis on the plurality of new clinical experiences by way of a sequence alignment algorithm, wherein the sequence alignment algorithm determines a mutation set for a specific clinical experience from the plurality of new clinical experiences;

determining a case progression for each of the plurality of the patient histories by way of a case progression prediction method;

determining a qualitative similarity value by initiating a pattern recognition algorithm;

selecting a medical future for each of the plurality of new clinical experiences; and displaying a treatment protocol based on the new clinical experience by performing a treatment probability prediction method.

10. The method for determining the case progression for a new clinical experience by executing computer executable instructions stored on a non-transitory computer readable medium, the method as claimed in claim 9 comprises the steps of:

receiving the new clinical experience, wherein the new clinical experience comprises the provided sequence, the reference sequence, a clinical information set, the treatment protocol, and the treatment outcome;

wherein the clinical information set comprises the list of signs and symptoms and the medical assessment;

initiating the sequence alignment algorithm in order to create a sequence alignment from the provided sequence and the reference sequence;

determining the mutation set from the sequence alignment, wherein the mutation set comprises a plurality of mutations; and initiating the case progression prediction method.

11. The method for determining the case progression for a new clinical experience by executing computer executable instructions stored on a non-transitory computer readable medium, the method as claimed in claim 9 comprises the steps of:

combining the new clinical experience and the mutation set of the sequence alignment to create a new search case;

searching for similar past cases within the database by comparing the new search case to the past case of each of the plurality of patient histories;

retrieving a similar patient history for each of the similar past cases from the database;

comparing the past case and the subsequent case for the similar patient history in order to determine the case progression the similar patient history by way of the case progression prediction method;

comparing the similar patient history against other similar patient histories in order to determine a qualitative similarity value for each of the other patient histories by way of the pattern recognition algorithm;

grouping the similar patient history into a plurality of corresponding histories by comparing the qualitative similarity value of the similar patient history against the qualitative similarity value of each of the other similar patient histories; and determining the medical future by comparing the new search case to the similar patient history.

12. The method for determining the case progression for a new clinical experience by executing computer executable instructions stored on a non-transitory computer readable medium, the method as claimed in claim 9 comprises the steps of:

determining a patient similar value for the similar patient case and for each of the other similar patient cases by comparing the new search case to the similar patient history and by comparing the new search case to each of the other similar patient histories, wherein the patient similar value is a weighted value reflecting similarities between the past case and the new search case;

calculating the treatment occurrence probability for the treatment protocol of the past case of each of the plurality of corresponding histories;

ranking the treatment protocol by the treatment probability for each of the plurality of corresponding histories in order to compile a list of ranked treatment protocols;

calculating the progression probability for the medical future of the similar patient history by comparing the case progression of the similar patient history against the case progression of the other similar patient histories and by weighing the case progression of each of the other similar histories with the patient similar value;

ranking the medical future by the progression probability for the similar patient history and for each of other similar patient histories in order to compile a list of ranked medical futures; and displaying the ranked list of the treatment protocols and the ranked list of medical futures.

\* \* \* \* \*